United States Patent
Ouchi

(10) Patent No.: US 6,582,450 B2
(45) Date of Patent: *Jun. 24, 2003

(54) ENDOSCOPIC MANIPULATING WIRE COUPLING STRUCTURE

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 249 days.

This patent is subject to a terminal disclaimer.

(21) Appl. No.: 09/726,339

(22) Filed: Dec. 1, 2000

(65) Prior Publication Data

US 2001/0041912 A1 Nov. 15, 2001

(30) Foreign Application Priority Data

Dec. 2, 1999 (JP) .......................................... 11-342735

(51) Int. Cl.[7] .............................................. A61B 17/28
(52) U.S. Cl. .................................................... 606/205
(58) Field of Search ....................... 606/205; 140/105; 24/715.4, 715, 715.7, 20 R

(56) References Cited

U.S. PATENT DOCUMENTS 5,524,327 A * 6/1996 Mickel et al. ............ 24/115 A
6,402,738 B1 * 6/2002 Ouchi ........................ 600/146

FOREIGN PATENT DOCUMENTS

JP 20000225121 8/2000

* cited by examiner

*Primary Examiner*—John J. Calvert
*Assistant Examiner*—James G Smith
(74) *Attorney, Agent, or Firm*—Greenblum & Bernstein, P.L.C.

(57) ABSTRACT

An endoscopic manipulating wire coupling structure is constructed such that an end of a manipulating wire including two or more twisted strands is inserted into an opening in a mating member which is plastically deformed from the outer circumference inward so that it is securely pressed against the manipulating wire. At least that portion of the mating member which is fitted over the manipulating wire is formed of a material softer than the manipulating wire.

10 Claims, 7 Drawing Sheets

FIGURE 12
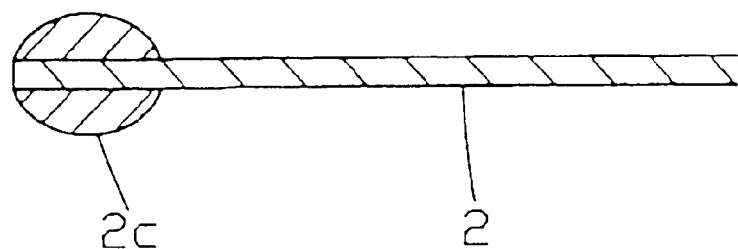
FIGURE 13
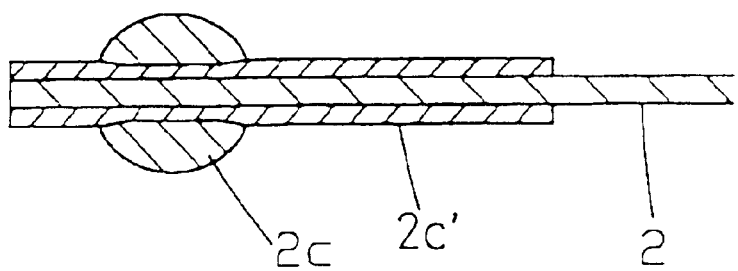
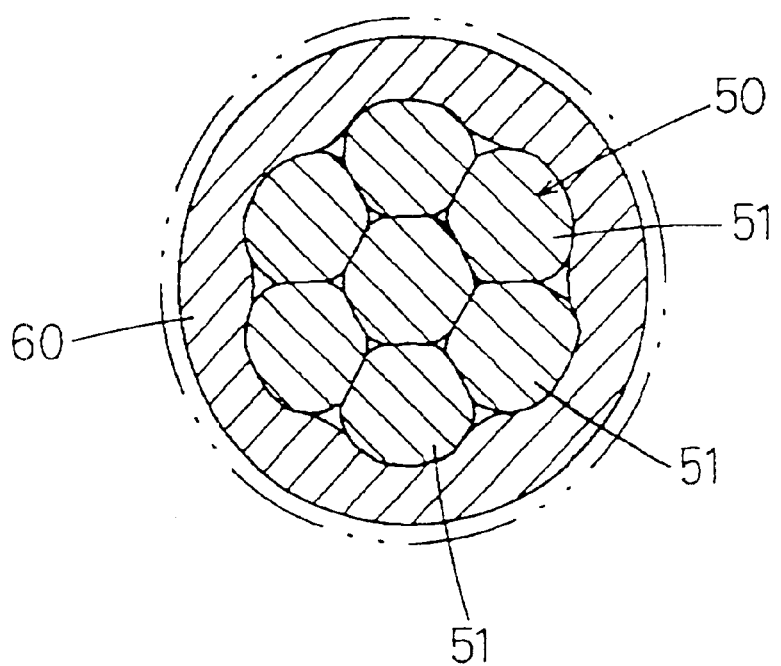
FIGURE 14

US 6,582,450 B2

ENDOSCOPIC MANIPULATING WIRE COUPLING STRUCTURE

BACKGROUND OF THE INVENTION

This invention relates to an endoscopic manipulating wire coupling structure.

Endoscopic manipulating wires are generally composed of two or more fine twisted metal stands so that they will not get prone to bend easily. An end of such endoscopic manipulating wire is inserted into an opening in a mating member and securely coupled to the latter by a suitable means such as brazing with sliver or soldering.

In the case of brazing with silver, the areas to be coupled of the two members need be heated up to about 600° C. To meet this need, a small burner is typically used as the heater but because of the heat capacity of the portions being heated, that part of the manipulating wire which is not inserted into the mating member is prone to become hotter than the other part which is inserted into the mating member.

This prevents the brazing silver from reaching every part of the areas that need be securely coupled. On the other hand, the silver flows out to the adjacent area of the manipulating wire which is not inserted into the mating member and the length of the rigid portion exceeds a design value or the manipulating wire may be oxidized to present a problem with strength.

In the case of soldering, the strength it can achieve is inherently low and if any of the flux used in the soldering operation remains unremoved, the strength it presents will decrease at a later time to increase the chance of discoupling between the manipulating wire and the mating member. To avoid this problem, the flux must be washed away from the coupled parts to but this is very cumbersome to achieve.

As an alternative method, an end of the manipulating wire may be inserted into an opening in the mating member which is then clamped to deform plastically from the outer circumference inward so that it is securely pressed against the manipulating wire.

If this method is simply applied, the force exerted to cause plastic deformation of the mating member 60 is also transmitted to the inwardly positioned manipulating wire 50 as indicated in FIG. 14, so that the individual strands 51 collapse to a smaller diameter and the resulting drop in strength increases the chance of wire breakage during service.

SUMMARY OF THE INVENTION

An object, therefore, of the present invention is to provide an endoscopic manipulating wire coupling structure by which a manipulating wire and a mating member can be securely coupled by a simple and positive operation while assuring consistent strength.

According to the invention, at least that portion of a mating member which is fitted over a manipulating wire is formed of a material softer than the manipulating wire, and deformed plastically from the outer circumference inward so that it is pressed to be securely coupled to the manipulating wire. Since this can be achieved without plastic deformation of the individual strands in the manipulating wire, the two members can be securely coupled together by a simple and positive operation while assuring consistent strength without reducing the diameter of the individual strands in the manipulating wire.

An endoscopic manipulating wire coupling structure of a preferred embodiment is generally constructed such that an end of a manipulating wire consisting of two or more twisted strands is inserted into an opening in a mating member which is plastically deformed from the outer circumference inward so that it is securely pressed against the manipulating wire. In the structure, at least that portion of the mating member which is fitted over the manipulating wire is formed of a material softer than the manipulating wire.

The mating member may be securely pressed against the manipulating wire at a plurality of sites spaced apart along the longitudinal axis. If desired, a tubular member formed of a material softer than the manipulating wire may be placed between the inner surface of the opening in the mating member and the manipulating wire inserted into the opening.

The manipulating wire may be used in an endoscopic treatment tool. Alternatively, it may be a curving manipulating wire in an endoscope.

The present disclosure relates to the subject matter contained in Japanese patent application No. Hei. 11-342735 (filed on Dec. 2, 1999), which is expressly incorporated herein by reference in its entirety.

BRIEF DESCRIPTION OF THE DRAWINGS

FIG. 12 is a side sectional view showing another example of the manipulating wire coupling section to be used with the curving portion of the endoscope;

FIG. 13 is a side sectional view showing yet another example of the manipulating wire coupling section to be used with the curving portion of the endoscope; and FIG. 14 is a front sectional view of a mating member coupled by claming to a conventional endoscopic manipulating wire.

DESCRIPTION OF THE PREFERRED EMBODIMENT

Preferred embodiments of the invention are described below with reference to accompanying drawings.

Figure 2:
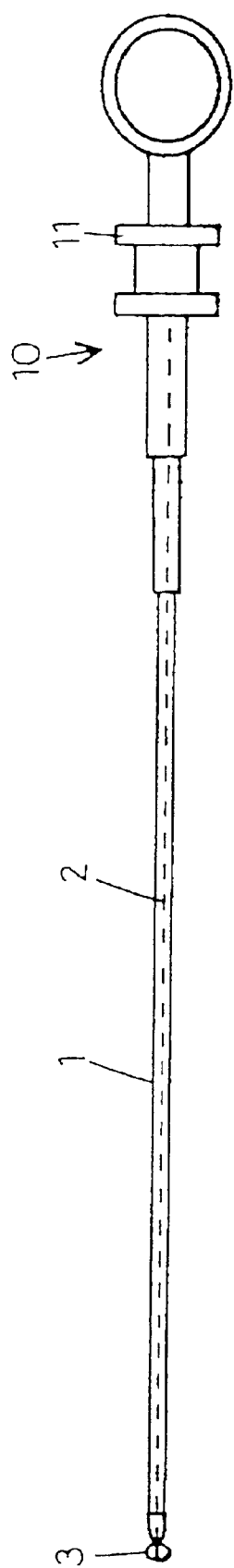
FIG. 2 is a side view showing the general construction of the endoscopic treatment tool.

FIG. 2 shows endoscopic biopsy forceps which is a typical endoscopic treatment tool. It comprises a flexible sheath 1 that is inserted into or removed from a treatment tool insertion channel (not shown) in an endoscope and which contains a manipulating wire 2 composed of twisted stainless steel strands in such a way that it extends over the entire length of the flexible sheath 1 to be capable of moving back and forth along the longitudinal axis.

A manipulating section 10 is coupled to the basal end of the sheath 1 and has a slider 11 as a manipulating member. By moving the slider 11 back and forth, a pair of forceps cups 3 provided at the distal end of the sheath 1 are driven via the manipulating wire 2 so that they open and close like beaks.

Figure 1:
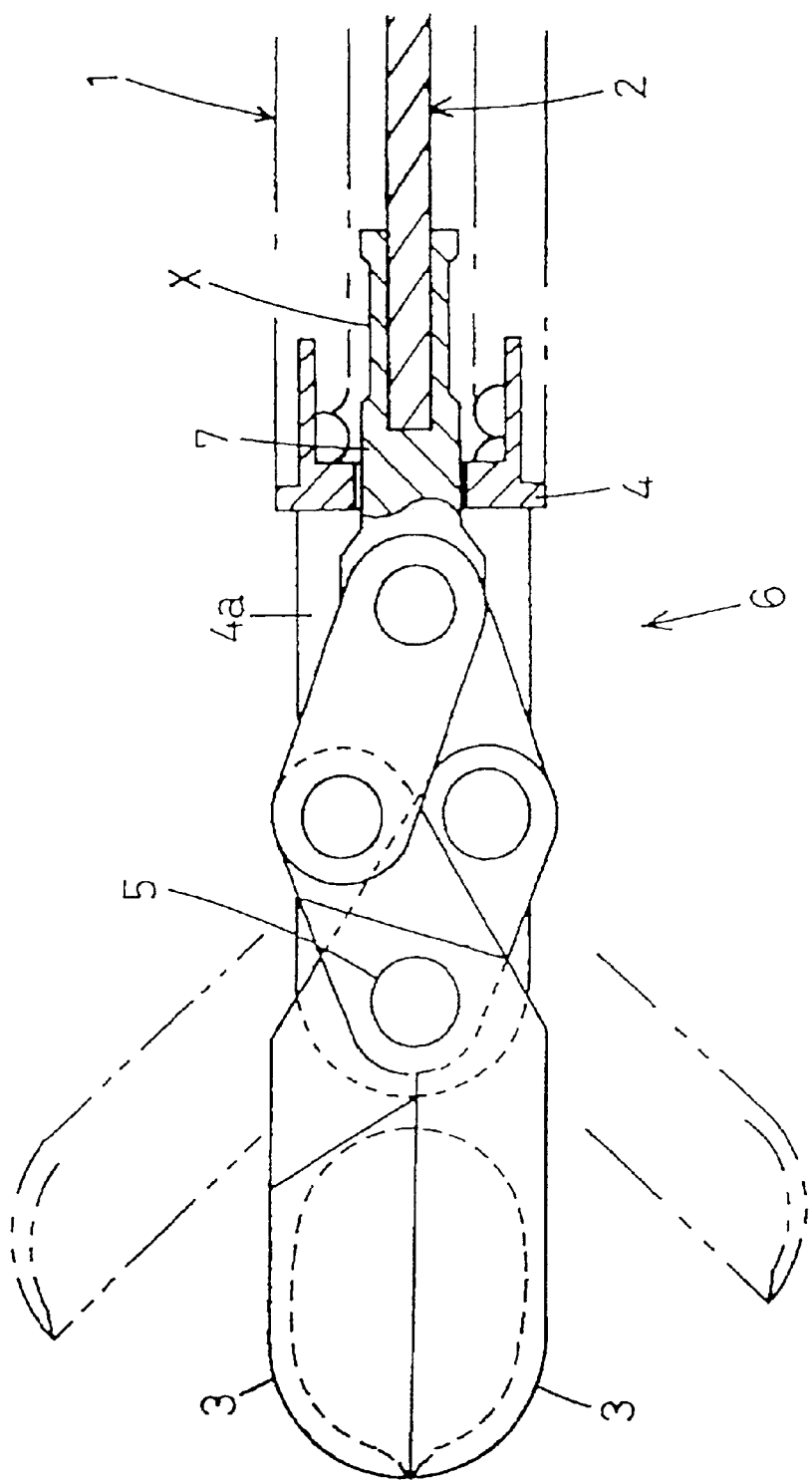
FIG. 1 is a side view showing in partial section the distal end portion of an endoscopic treatment tool according to the first mode of carrying out the present invention.

FIG. 1 shows the distal end portion of biopsy forceps. A distal end support body 4 is securely coupled to the distal end of the sheath 1 and has a slot 4a formed to open to the front end. A support pin 5 provided to traverse the slot 4a supports the pair of forceps cups 3 in such a way that they are free to open and close like beaks.

A link mechanism 6 for activating the forceps cups 3 to open and close is provided within the slot 4a and has a mating member 7 pinned to the rear end. The distal end of the manipulating wire 2 is securely coupled to the mating member 7.

Figure 3:
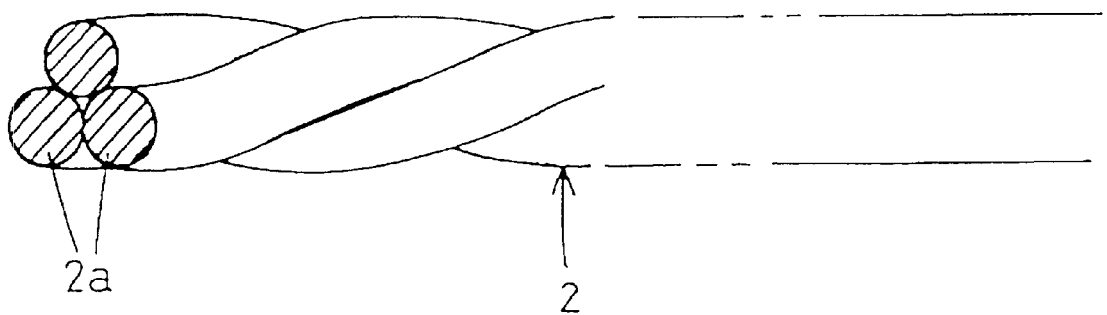
FIG. 3 is a side view of a manipulating wire consisting of three twisted strands (1×3 system), together with a cross section of the wire as it is seen from the front.
Figure 4:
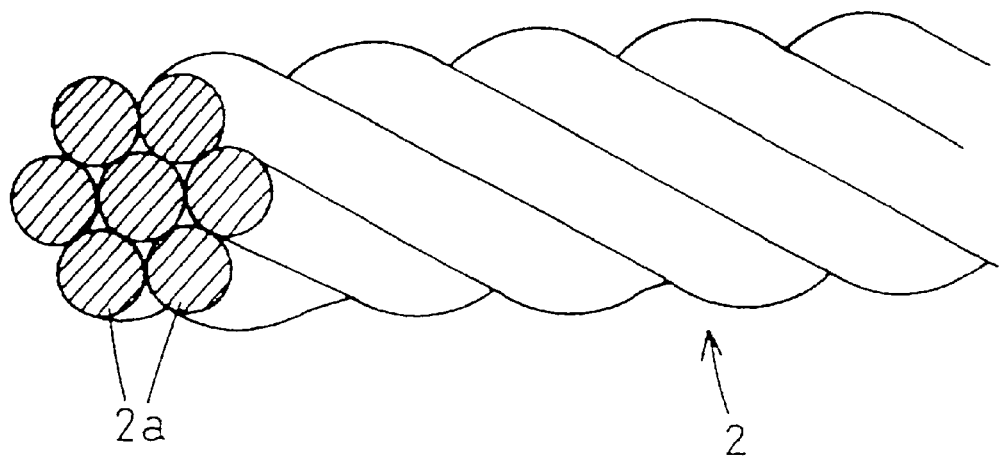
FIG. 4 is a side view of a manipulating wire consisting of seven twisted strands (1×7 system), together with a cross section of the wire as it is seen from the front.
Figure 5:
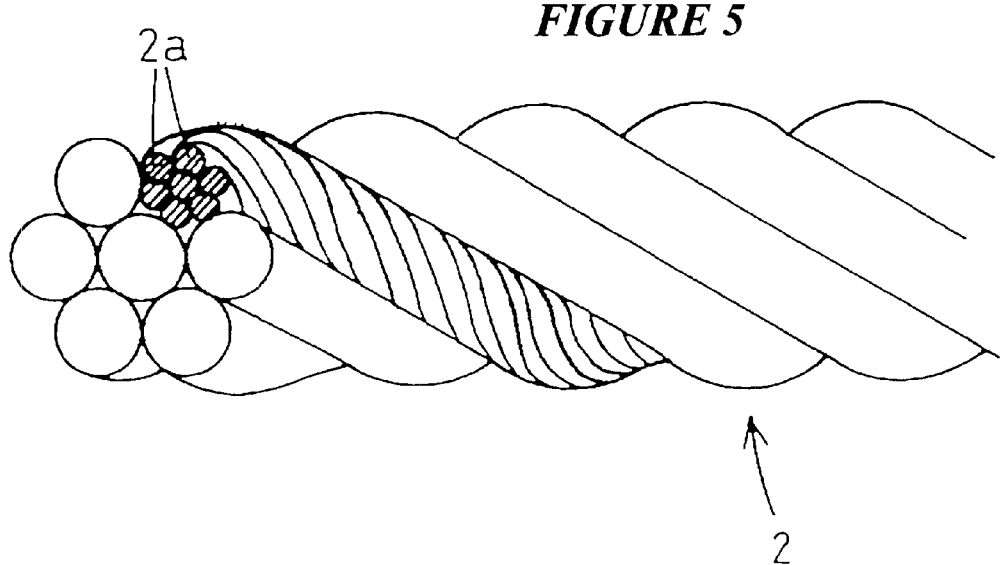
FIG. 5 is a side view of a manipulating wire consisting of seven twisted units each consisting of seven twisted strands (7×7 system), together with a cross section of the wire as it is seen from the front.

The manipulating wire 2 is formed of twisted strands of fine stainless steel wires. FIG. 3 shows a 1×3 system consisting of three such twisted strands 2a; FIG. 4 shows a 1×7 system consisting of seven such twisted strands 2a; and FIG. 5 shows a 7×7 system in which seven units each consisting of seven such twisted strands 2a are further twisted together (the system is shown partly omitted in FIG. 5). The manipulating wire 2 may adopt either one of these systems or any other systems of twisted strands.

Turning back to FIG. 1, the mating member 7 is formed of a copper alloy, a gold alloy or any other material that is softer (less harder) than the stainless steel of which the manipulating wire 2 is made. The mating member 7 has an opening in the rear part which is formed in a cylindrical shape and the distal end portion of the manipulating wire 2 is inserted into this opening.

That part of the mating member 7 which receives the manipulating wire 2 is clamped from the outside so that it deforms plastically to a smaller diameter and in the resulting clamped area X, the mating member 7 is securely pressed and coupled to the manipulating wire 2.

Since the mating member 7 is formed of a softer material than the manipulating wire 2, it can be clamped to deform plastically by an insufficient force to cause plastic deformation of the manipulating wire 2 and this allows the two members to be coupled together without reducing the strength of the manipulating wire 2 in the coupled area.

Figure 6:
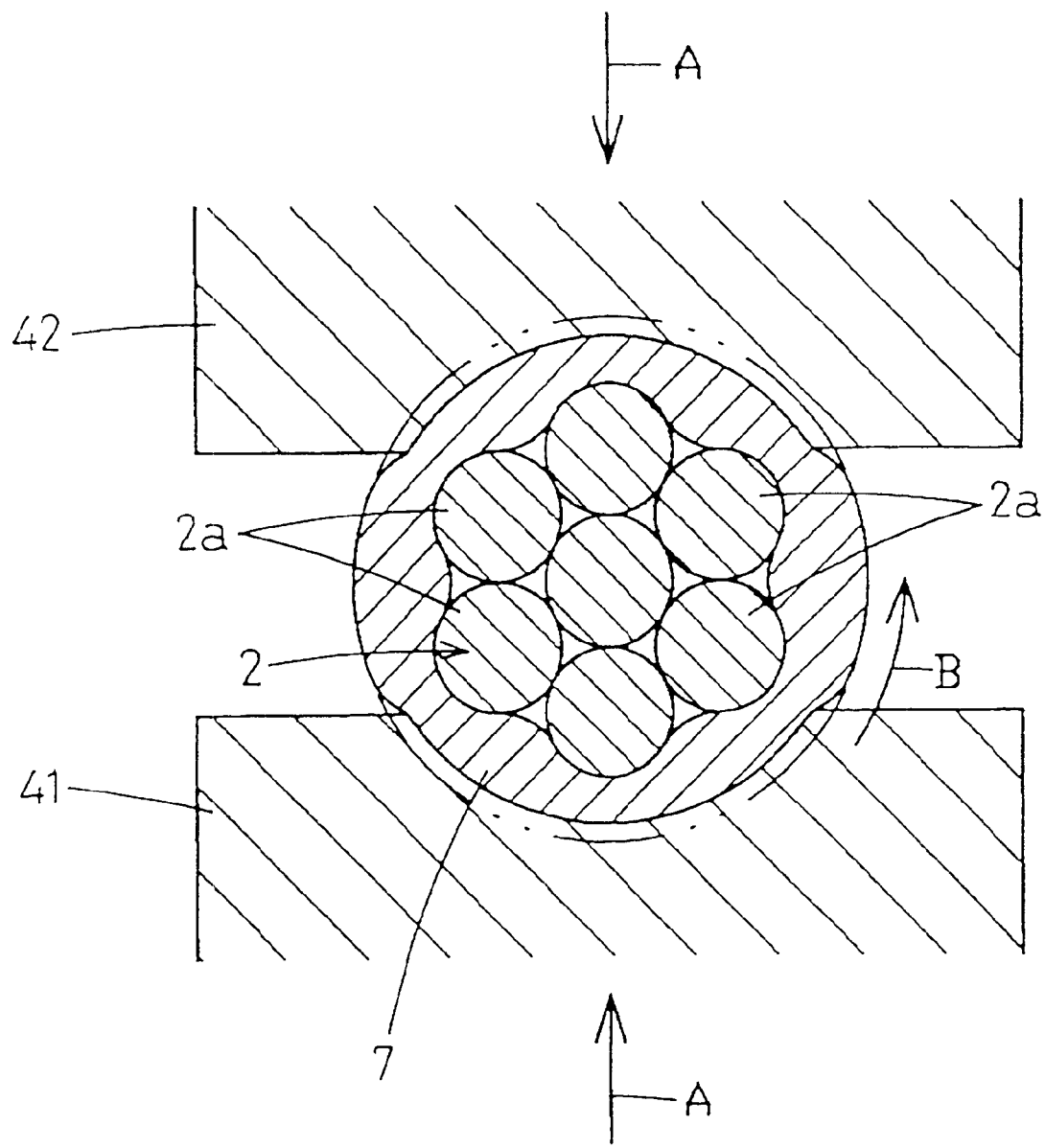
FIG. 6 is a front sectional view of a mating member as it has been clamped to provide secure coupling to a manipulating wire according to the first mode of carrying out the invention.

An exemplary method of clamping the mating member 7 is shown in FIG. 6. The mating member 7 is placed between a pair of opposed clamping tools 41 and 42 and pressed or otherwise subjected to a force in the direction of arrow A which is sufficient to deform it plastically but insufficient to cause plastic deformation of the manipulating wire 2; thereafter, the mating member 7 is rotated through a desired angle about the longitudinal axis (in the direction of arrow B) and subjected to the clamping action. This procedure is repeated several times.

As a result of this clamping process, the mating member 7 deforms plastically and gets into the gaps between strands 2a in the manipulating wire 2; however, the strands 2a do not deform but retain their initial shape so that the strength of the manipulating wire 2 remains the same. It suffices for the purpose of the present invention if at least that portion of the mating member 7 which is fitted over the manipulating wire 2 is formed of a material softer than the latter.

Figure 7:
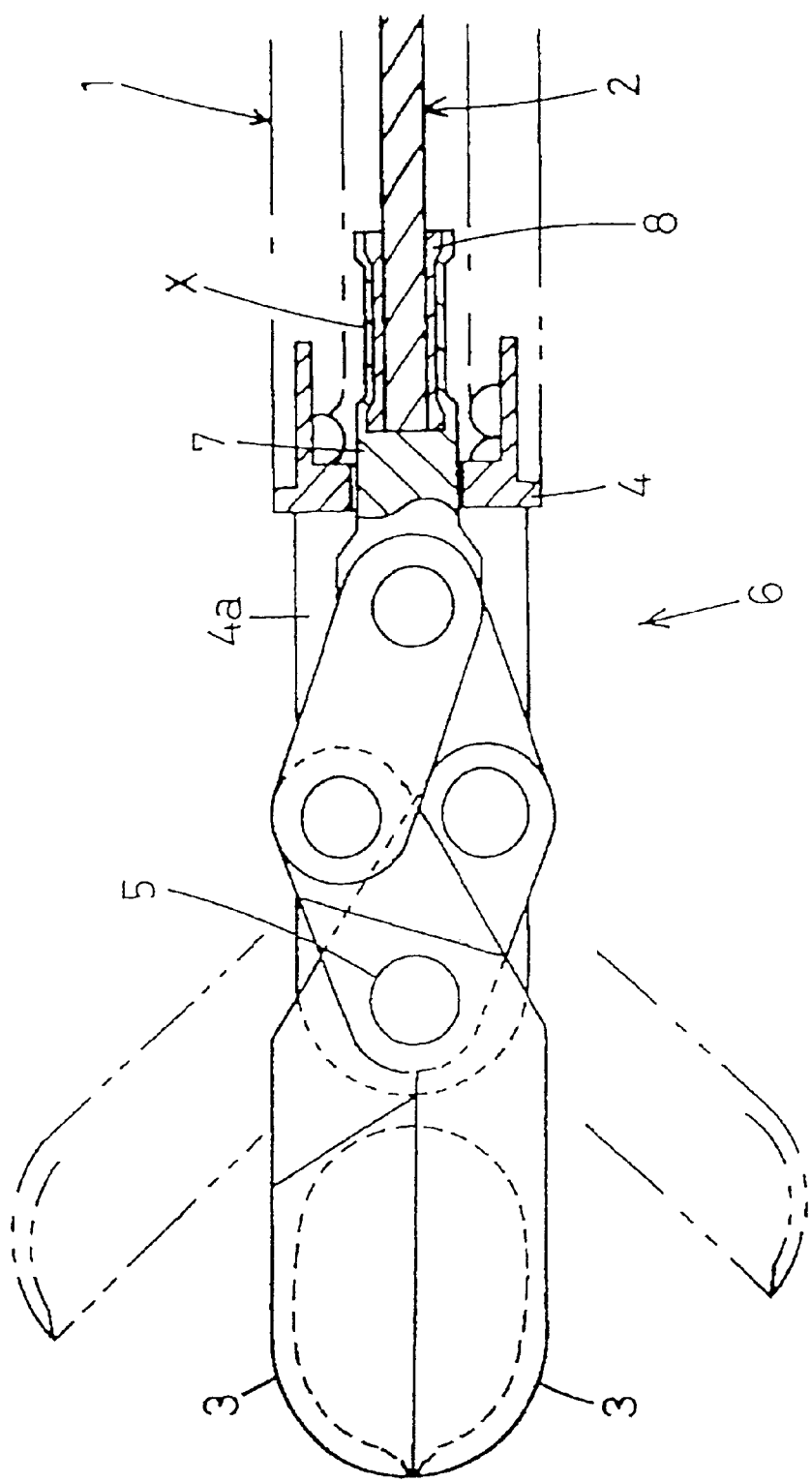
FIG. 7 is a side view showing in partial section the distal end portion of an endoscopic treatment tool according to the second mode of carrying out the present invention.

As shown in FIG. 7, a sleeve 8 made of a material softer than the manipulating wire 2 may be placed between the mating member 7 and the manipulating wire 2 before the mating member 7 is clamped from the outside. The strands 2a in the manipulating wire 2 do not deform plastically but the sleeve 8 as well as the mating member 7 undergo plastic deformation and as in the case shown in FIG. 1, an end portion of the manipulating wire 2 can be firmly coupled is to the mating member 7.

In the above-described embodiment, the concept of the invention is applied to the distal end portion of the manipulating wire 2 for endoscopic biopsy forceps. Alternatively, as shown in FIG. 8, the concept of the invention may be applied to the biopsy forceps manipulating section 10, particularly for the purpose of establishing secure coupling of the basal end portion of the manipulating wire 2.

Figure 9:
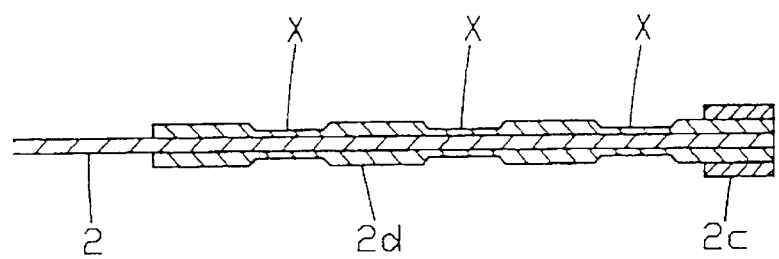
FIG. 9 is a side sectional view of the manipulating wire coupling portion of an endoscopic treatment tool according to the third mode of carrying out the present invention.

FIG. 9 shows this alternative case in which the basal rather than distal end portion of the manipulating wire 2 is securely coupled. The manipulating wire 2 is passed through a fine pipe 2d that has a lock member 2c secured to an end by brazing with silver or some other means and the pipe 2d is clamped at several sites X so that it deforms plastically to a smaller diameter. The pipe 2d is formed of a material softer than the manipulating wire 2 and the stands 2a in the manipulating wire 2 do not deform plastically.

Figure 8:
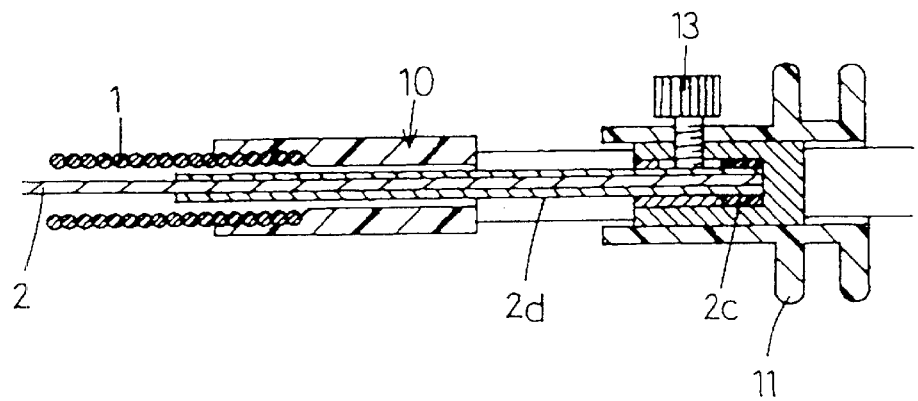
FIG. 8 is a side view showing in partial section the manipulating section of an endoscopic treatment tool according to the third mode of carrying out the present invention.

With its basal end portion being thus constructed, the manipulating wire 2 is secured to the slider 11 by tightening a manual screw 13 as shown in FIG. 8. To disengage the manipulating wire 2 from the slider 11, the manual screw 13 may be loosened. If desired, the manipulating wire 2 may be secured to the slider 11 and other parts by direct coupling. The pipe 2d may be clamped in only one area X.

The effectiveness of the concept of the invention is not limited to biopsy forceps alone; it is equally applicable to various other endoscopic treatment tools in which the sheath 1 is separable from the manipulating section 10.

Figure 10:
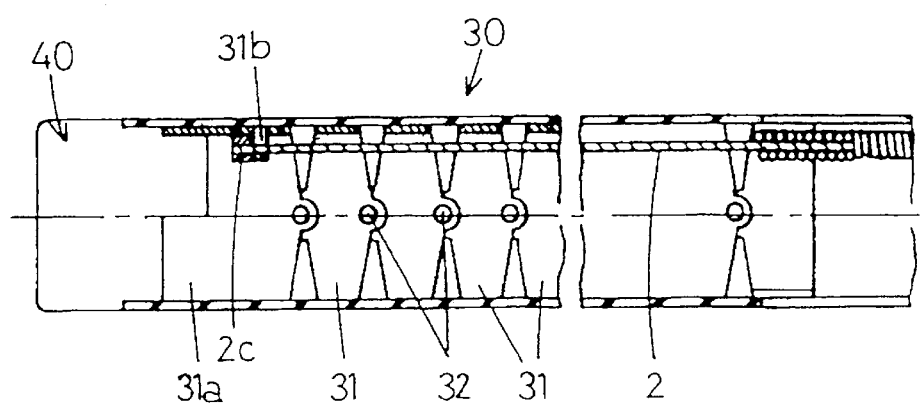
FIG. 10 is a side sectional view of a curving portion of an endoscope according to the fourth mode of carrying out the present invention.

Great utility is also achieved by applying the concept of the invention to an endoscope per se. FIG. 10 shows a curving section 30 provided at the distal end of the insertion portion of an endoscope. It is composed of two or more (typically about 5–15) annular segments 31 that are pivotally coupled together by means of rivets 32. A functional tip 40 having built-in objective optics and the like (not shown) is coupled to the foremost annular segment 31a.

The manipulating wire 2 having a lock member 2c fixed to the distal end is passed through an orifice 31b made in the inner surface of the fore most annular segment 31a and it extends backward. If the operator pulls the manipulating wire 2 via the manipulating section (not shown) connected to the basal end of the insertion portion of the endoscope, the curving section 30 bends accordingly.

Figure 11:
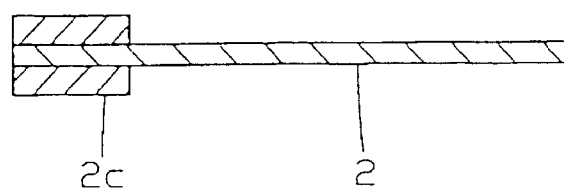
FIG. 11 is a side sectional view showing an example of the manipulating wire coupling section to be used with the curving portion of the endoscope.

FIG. 11 shows how the lock member 2c made in a cylindrical form of a material softer than the manipulating wire 2 is clamped to the distal end of the manipulating wire 2. Note that the whole length of the lock member 2c is clamped.

If desired, the lock member 2c may be of a spherical form as shown in FIG. 12. In this case, a pipe 2c' made of a material softer than the manipulating wire 2 may be inserted between the spherical lock member 2c and the manipulating wire 2.

What is claimed is:

1. An endoscopic manipulating wire coupling structure in which an end of a manipulating wire formed of two or more twisted strands is inserted into an opening in a mating member which is plastically deformed from the outer circumference inward so that it is securely pressed against said manipulating wire, wherein at least that portion of said mating member which is fitted over said manipulating wire is formed of a material softer than said manipulating wire.

2. The endoscopic manipulating wire coupling structure according to claim 1, wherein said mating member is securely pressed against said manipulating wire at a plurality of sites spaced apart along the longitudinal axis.

3. The endoscopic manipulating wire coupling structure according to claim 1, wherein a tubular member formed of a material softer than said manipulating wire is placed between the inner surface of the opening in said mating member and said manipulating wire inserted into said opening.

4. The endoscopic manipulating wire coupling structure according to claim 1, wherein said manipulating wire is used in an endoscopic treatment tool.

5. The endoscopic manipulating wire coupling structure according to claim 1, wherein said manipulating wire is a curving manipulating wire in an endoscope.

6. An endoscopic manipulating wire coupling method comprising the steps of:

fitting a portion of a mating member over an end portion of a manipulating wire formed of two or more twisted strands, said portion of the mating member being softer than said end portion of the manipulating wire;

applying pressure onto the outer circumference of said portion of the mating member to cause plastic deformation of said portion of the mating member and elastic deformation of said end portion of the manipulating wire but not to cause plastic deformation of said manipulating wire.

7. The endoscopic manipulating wire coupling method according to claim 6, wherein the pressure is applied onto the outer circumference of said portion of the mating member at a plurality of sites spaced apart along the longitudinal axis.

8. The endoscopic manipulating wire coupling method according to claim 6, further comprising:

interposing a tubular member between said portion of the mating member and said end portion of the manipulating wire prior to said step of applying pressure, the tubular member being softer than the manipulating wire.

9. The endoscopic manipulating wire coupling method according to claim 6, further comprising:

providing a tubular member on and around said end portion of the manipulating wire prior to said step of fitting, the tubular member being softer than the manipulating wire.

10. The endoscopic manipulating wire coupling method according to claim 6, further comprising:

providing a tubular member on and around an interior of said portion of the mating member prior to said step of fitting, the tubular member being softer than the manipulating wire.

* * * * *